United States Patent
Staab

[11] 4,156,812
[45] May 29, 1979

[54] PNEUMATIC RADIATION DETECTOR

[75] Inventor: Joachim Staab, Frankfurt am Main, Fed. Rep. of Germany

[73] Assignee: Hartman & Braun Aktiengesellschaft, Frankfurt am Main, Fed. Rep. of Germany

[21] Appl. No.: 867,589

[22] Filed: Jan. 6, 1978

[51] Int. Cl.² .............................................. G01J 1/00
[52] U.S. Cl. .................................................. 250/345
[58] Field of Search ....................... 250/343, 344, 345

[56] References Cited
U.S. PATENT DOCUMENTS
3,725,702   4/1973   Schaefer .............................. 250/343

Primary Examiner—Alfred E. Smith
Assistant Examiner—Janice A. Howell
Attorney, Agent, or Firm—Smyth, Pavitt, Siegemund, Jones & Martella

[57] ABSTRACT

A two beam radiation detector has two gas systems in a metal block. Each system has two detection chambers, one per incident radiation beam, and two chambers, pertaining to different systems, are traversed by the same beam. The two systems further include a common, but biparted, pressure difference sensing chamber containing a flexible membrane.

4 Claims, 1 Drawing Figure

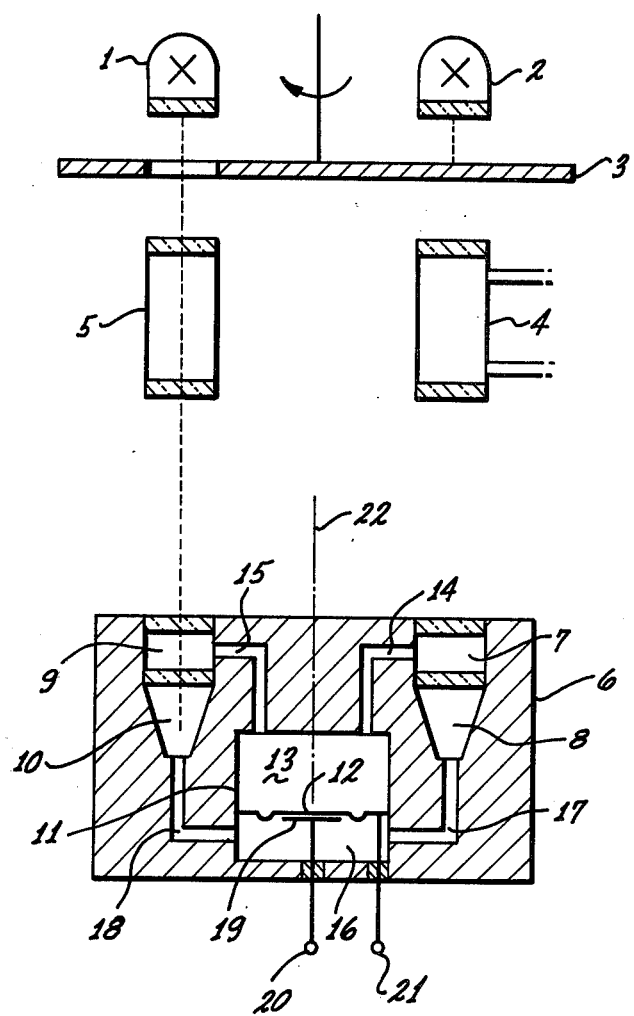

PNEUMATIC RADIATION DETECTOR

BACKGROUND OF THE INVENTION

The present invention relates to a pneumatic radiation detector, particularly for infrared gas analysis.

A typical detector of the kind to which the invention pertains operates with two chopped (modulated) beams of infrared radiation, whereby the chopper provides the modulation in phase opposition as to the two beams. The detector is provided with two chambers for each beam, which are traversed by the respective beam serially or sequentially. These chambers are filled with particular gas and the first one of the chambers in each path has an entrance and an exit window, the respective other chambers may have only an entrance window, but it also may have an exit window. Two of the chambers in different beam paths are, for example, gas-conductively connected to opposite subchambers of a particular chamber which is biparted by a membrane, being the displaceable electrode of a variable capacitor. Pressure differences in the two subchambers are translated into an electrical signal by this capacitor. A typical device of the type referred to above is shown, for example, in US-Letters Pat. No. 3,725,702.

It was found that mechanical vibrations, impacts or other interferences may cause the membrane to vibrate, either directly or by operation of unwanted oscillatory movements of gas. Shocks may also alter the zero or any other reference point in this detector.

DESCRIPTION OF THE INVENTION

It is an object of the present invention to improve radiation detectors of the type outlined above, particularly in regard to zero point stability and in further, more general regard, to the effects of externally induced or imparted shocks, impacts, and other vibrations or vibration-like mechanical interferences.

In accordance with the preferred embodiment of the present invention, it is suggested to construct a detection chamber assembly including a biparted chamber with a flexible membrane, such that a first gas system as a whole and as communicating with and including one part of the biparted chambers, has a center of gravity which coincides with the center of gravity of a second gas system, which communicates with and includes the other part of the biparted chamber. Each gas system includes two detection chambers, one per beam path, whereby the chambers of one system are both traversed by the beams before the beams respectively traverse the detector chamber of the other beam. Each system further includes conduit means for connecting the chambers to one part of the biparted pressure differential sensing chamber.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which: The FIGURE illustrates somewhat schematically a cross-section through an infrared detector system improved in accordance with the preferred embodiment of the invention.

Proceeding now to the detailed description of the drawing, the FIGURE shows two sources of infrared radiation, 1 and 2, which, respectively, emit two parallel beams of such radiation. A chopper wheel 3, possibly having alternating segments for passing and blocking radiation, modulates the two beams in base opposition.

The beam emitted by source 1 and after having been modulated, traverses a chamber 5 being filled with a reference gas or having been evacuated. The chamber 5 has an entrance and an exit window physically sealing the chamber, but this beam passes through and becomes the reference beam. The beam emitted by source 2, also after modulation, traverses a vessel or chamber 4, which is passed through by test gas to be analyzed. The chamber 4 has also an entrance and an exit window, and the test beam leaves the latter.

The detector proper is contained in a metal block 6 which contains two serial detector chambers 9 and 10 for the reference beam, and two serial chambers 7 and 8 for the test beam. The several detector chambers have windows, whereby the entrance windows for chambers 8 and 10 constitute also the exit windows for chambers 7 and 8. All windows are, of course, sealed.

Another chamber 11 is centrally disposed in block 6 which chamber is actually biparted by a flexible membrane 12 to establish two separate chambers or chamber parts, 13 and 16. Together they establish a pressure differential chamber. Chamber 13 is gas-conductively connected to chamber 7 via a conduit 14, and to chamber 9 via a conduit 15. These chambers 7, 9 and 13 together with conduits 14 and 15 establish a first gas system. The other chamber 16 is analogously connected to chambers 8 and 10 via ducts 17 and 18, respectively. These chambers and conduits 8, 10, 16, 17 and 18 establish a second gas system. Chamber 16 contains also a stationary electrode 19 being the counter electrode for flexible electrode 12; these electrodes together constitute a measuring, pick-up or detecting capacitor, which converts pressure differentials between chambers 13 and 16 into electrical signals. These signals are derivable from terminals 20 and 21 which connect to the two electrodes.

The two chambers 8 and 10 have a conical contour for reasons of radiation physics. All detector chambers are arranged and are dimensioned so that the common center of gravity of the gas in the two chambers 7 and 9, and in the chamber 13 connected to them, coincides with the center of gravity of the gas in chambers 8, 10 and 16. In other words, the two gas systems as defined have coinciding centers of gravity. Preferably, that common center of gravity is disposed in a plane 22 of symmetry of the detector which also halves the capacitor. It was found that this way shocks or other externally introduced vibrations do not cause gas flow oscillations in the system, which will stimulate the membrane 12 to undergo parasitic vibrations.

The invention is not limited to the embodiments described above but all changes and modifications thereof not constituting departures from the spirit and scope of the invention are intended to be included.

I claim:

1. In a pneumatic type radiation detector for receiving two beams of infrared radiation, the detector including gas-filled radiation absorption chambers and a differential chamber biparted by a flexible membrane, some of the chambers being connected to one part of the differential chamber, others of the chambers being connected to the other part of the differential chambers to thereby establish two gas systems, the improvement comprising the two gas systems having a common center of gravity.

2. In a detector as in claim 1, wherein each gas system includes two detector chambers, respectively traversed by the two beams, whereby the two detector chambers of one of the systems are respectively traversed by beams before the beams traverse the two detector chambers of the other one of the gas systems.

3. In a detector as in claim 2, wherein said chambers are contained in a common block.

4. In a pneumatic type radiation detector for receiving two beams of radiation, having a first pair of gas-filled detector chambers, serially arranged in the path of one of the beams, and a second pair of gas-filled detector chambers serially arranged in the path of the other one of the beams, the chambers being in a common block which also contains a pressure difference sensing chamber, being biparted by a flexible membrane constituting a capacitor electrode, the improvement comprising:

first conduit means for connecting the two chambers of the two pairs being traversed first by the two beams, to one part of the biparted chamber;

second conduit means for connecting the other chambers of the two pairs to the other part of the biparted chamber; and said chambers and said conduit means being so dimensioned so that the two chambers and the part of the biparted chamber as interconnected by the first conduit means and the first conduit means together have a center of gravity for the gas they contain, which coincides with the center of gravity of the gas contained in the other two chambers and the other part of the biparted chamber as interconnected by the second conduit means and in the second conduit means.

* * * * *